United States Patent [19]

Klenk et al.

[11] Patent Number: 4,834,971
[45] Date of Patent: May 30, 1989

[54] HAIR PERMANENT-WAVING METHOD AND AFTERTREATMENT COMPOSITION

[75] Inventors: Adolf Klenk, Greverbroich; Detlef Hollenberg, Hilden; Horst Hoeffkes, Duesseldorf, all of Fed. Rep. of Germany

[73] Assignee: Henkel Kommanditgesellschaft auf Aktien, Duesseldorf, Fed. Rep. of Germany

[21] Appl. No.: 82,012

[22] Filed: Aug. 5, 1987

[30] Foreign Application Priority Data

Aug. 16, 1987 [DE] Fed. Rep. of Germany ....... 3627746

[51] Int. Cl.$^4$ .................... A61K 7/06; A61K 7/09; A61K 7/11
[52] U.S. Cl. ........................... 424/70; 424/71; 514/880
[58] Field of Search ............. 424/70, 71, 101; 514/880

[56] References Cited

U.S. PATENT DOCUMENTS 3,266,933  8/1966  Reiss et al. ............... 167/87.1
4,660,580  4/1987  Hoch et al. ................ 424/70
4,725,282  2/1968  Hoch et al. ................ 424/70

FOREIGN PATENT DOCUMENTS 680599   11/1966  Belgium .
0114414  12/1983  European Pat. Off. .
0134452   7/1986  European Pat. Off. .
2024623   1/1980  United Kingdom ............... 424/70

OTHER PUBLICATIONS

Japanese 60/100 512 Chemical Abstract; First Solution for Permanent Wave, 12-10-83, Seiyaku et al.; Japanese 60/158 105 Chemical Abstract; Hair Rinses containing organic acids, 01-28-84, Susumu et al.

*Primary Examiner*—Ellis P. Robinson
*Assistant Examiner*—P. J. Ryan
*Attorney, Agent, or Firm*—Ernest G. Szoke; Wayne C. Jaeschke; Norvell E. Wisdom

[57] ABSTRACT

A method for the permanent shaping of hair, in which the hair is treated with an aqueous preparation of a keratin-reducing substance before and/or after a mechanical shaping step, rinsed with water and fixed by treatment with an aqueous preparation of an oxidizing agent and rinsed with water, wherein, after the oxidative fixing step, the mechanically shaped hair is aftertreated with an aqueous composition comprising a dissolved aluminium (III) salt and a hydroxydi- or tri-$C_{4-6}$-carboxylic acid; the novel composition itself; and a kit for effecting such method.

16 Claims, No Drawings

HAIR PERMANENT-WAVING METHOD AND AFTERTREATMENT COMPOSITION

BACKGROUND OF THE INVENTION

1. Field of the Invention

This invention relates to a method for the permanent waving of hair by reductive cleavage and oxidative reformation of disulfide bonds of the hair keratin, in which the waving effect is enhanced by aftertreatment with a novel composition containing an aluminum (III) salt and a $C_{4-6}$ hydroxydi- or tri-carboxylic acid.

2. Statement of Related Art

In known permanent waving methods, the permanent shaping of hair is achieved by mechanically shaping the hair and fixing the applied shape, for example by winding onto hair curlers or rollers. Before and/or after this shaping step, the hair is treated with an aqueous preparation of a keratin-reducing substance, rinsed with water after a short contact time, and then treated in a second step with an aqueous preparation of an oxidizing agent. After a suitable contact time, the oxidizing agent is also rinsed out of the hair and the mechanical shaping aids (curlers, rollers) removed from the hair.

The aqueous preparation of the keratin reducing agent is normally alkalized to a considerable degree in order to swell the hair, thus enabling the keratin-reducing substance to penetrate deeply into the hair. The keratin-reducing substance cleaves some of the disulfide bonds of the keratin to —SH groups, so that the peptide network is loosened and the keratin structure is reoriented under the strain applied to the hair by the mechanical shaping treatment. Under the influence of the oxidizing agent, disulfide bonds are reformed and the keratin structure is thus refixed in the predetermined shape.

Neither the swelling effect of the alkali nor the keratin-splitting effect of the reducing agent can be completely neutralized, so that freshly permanently waved hair is extremely sensitive to mechanical stressing. Excessive reduction, for example through an excessive concentration of keratin-reducing substance or an overly long contact time, can also lead to severe hair damage, resulting in cosmetically undesirable overcurling of the hair.

It would be extremely desirable to provide a process for the permanent shaping of hair, in which the risk of unwanted side effects is avoided with greater certainty and in which the hair is less heavily stressed. Such a possibility would exist if it were possible to reduce the concentration of the keratin-reducing substance in the reduction step and to enhance shaping of the hair by less hair-damaging measures.

According to U.S. Pat. No. 3,266,994, a water-soluble magnesium, aluminium or calcium salt is added to the oxidative fixing solution. U.S. Pat. No. 3,981,312 describes a process for the permanent shaping of hair in which the hair is treated between the reduction step and the oxidative fixing step with a setting solution containing a polyvalent metal salt in aqueous solution. Finally, U.S. Pat. No. 4,409,204 describes an aftertreatment preparation for permanently waved hair which contains glyoxylic acid and certain unsaturated carboxylic acids. These measures were intended in themselves to counteract the loss of strength of the hair as a result of the permanent waving treatment. However, no satisfactory improvement was achieved through the measures mentioned.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that the structure and strength of permanently waved hair may be considerably improved by an aftertreatment carried out immediately after the oxidative fixing step, using the novel aqueous compositions containing at least one dissolved aluminium (III) salt and at least one hdyroxydi- or tri-carboxylic acid.

Accordingly, the present invention provides a variation of the known method for the permanent shaping of hair, in which: (A) the hair is treated by applying an aqueous composition comprising an effective amount of a keratin-reducing substance before and/or after (B) a mechanical shaping step; (C) the hair thus treated is rinsed with water after a certain contact time; (D) is fixed by treatment with an aqueous composition comprising an effective amount of an oxidizing agent; and (F) the hair thus treated is rinsed with water after a certain contact time. In the inventive method, after the oxidative fixing step (D), the mechanically shaped hair is (E) aftertreated with a novel aqueous composition consisting essentially of at least one dissolved aluminium (III) salt and at least one hydroxydi- or tri-$C_{4-6}$-carboxylic acid, after which (G) the mechanial shaping aids (hair curlers, rollers, etc., of step (B)) are removed.

The method according to the invention improves the result of the hair shaping treatment to such an extent that less concentrated preparations of the potentially harmful keratin reducing agent and/or shorter contact times of the potentially harmful reducing agent still lead to highly satisfactory hair shaping results. It is possible in this way to obtain enhanced shaping of hair without harming the hair or affecting its natural strength.

The keratin-reducing substances used in the inventive method are known and may be any of the usual mercaptans and/or the alkali salts of sulfurous acid. The alkali or ammonium salts of thioglycolic acid and/or thiolactic acid are particularly suitable for use in the inventive method. They may be used in concentrations of from 0.5 to 1.0 mol/kg in the keratin-reducing preparations of step (A) of the hair waving method according to the invention, at a pH of from 6.5 to 10. The conventional contact time for the keratin-reducing preparation is generally 20 to 40 minutes. Factors affecting the contact time include the thickness of the hair to be treated, the desired degree of shaping, the size of the mechanical shaping aids (hair curlers) used, and the nature of the keratin reducing agent. This conventional contact time may be reduced by 10 to 50% with the method and composition of aftertreatment according to the invention, for otherwise the same working conditions.

In addition to the keratin-reducing agent, the aqueous preparation step (A) of the hair shaping process according to the invention may contain any of the auxiliaries and additives known from this purpose. These include surfactants, complexing agents, ammonia and buffer salts (to adjust to a pH value of from 6.5 to 10, for example ammonium carbonate), urea, glycerol, water-soluble polymers for increasing viscosity, perfumes, dyes and opacifiers. Any known such ingredients may be used, provided only that they are compatible with the utility of this invention and the other ingredients.

The aqueous preparation for step (D), namely the oxidative fixing step, may contain hydrogen peroxide as an oxidizing agent and such compatible stabilizers as are conventionally used to stabilize aqueous hydrogen peroxide preparations. The pH value of aqueous $H_2O_2$ preparations such as these, which normally contain from about 0.5 to 3.0% by weight $H_2O_2$, is preferably from 2 to 4 and is adjusted by inorganic acids, preferably phosphoric acid. The preferred oxidizing agent is sodium or potassium bromate. The bromates are used in concentrations of from 1 to 10% by weight and the pH value of the solutions is adjusted to between 4 and 7.

In addition to the oxidizing agent, the aqueous preparation for step (D) may contain other auxiliaries and additives known for this purpose, including surfactants, quaternary ammonium salts, cationic polymers, water-soluble proteins or protein derivatives, perfumes and opacifiers. Any known such ingredients may be used, provided only that they are compatible with the utility of this invention and the other ingredients.

The aqueous preparations for step (A) and/or (D), as well as the aqueous aftertreatment compositions of step (E) may be provided in conventional aerosol dispensers, hand-operated sprays, comb or brush applicators, or the like.

The aqueous composition (E) for carrying out the aftertreatment contains as critical components: (1) at least one dissolved aluminium (III) salt, and (2) at least one hydroxydi-$C_{4-6}$-carboxylic acid or hydroxytri-$C_{4-6}$-carboxylic acid. Useful aluminium (III) salts include: $AlCl_3$; $AlCl_3$; . 6 $H_2O$; $Al_2(SO_4)_3$; $Al_2(SO_4)_3 18 H_2O$; $AlNA(SO_4)_2$ . 12 $H_2O$; $Al(NH_4)(SO_4)_2$ . 12 $H_2O$; and other watersoluble aluminium salts, for example aluminium lactate; aluminium acetate; or aluminium salts of other organic carboxylic acids. The aluminium (III) salt is used in a quantity of from 10 to 1000 mmols/kg, expressed as Al. Preferred aluminum (III) salts are inorganic, $AlCl_3$ and $Al(SO_4)_3$ being more preferred. The aluminum (III) salts are added to the aqueous composition in a total quantity of 0.2 to 5%, preferably 1 to 4%, most preferably 2 to 3%, by weight, based on the total weight of the aftertreatment composition. $AlCl_3$ is particularly suitable, being used in the aqueous preparation in a quantity of 0.2 to 5%, preferably 1 to 4%, by weight.

Malic acid, tartaric acid and citric acid are suitable hydroxydi- or tricarboxylic acids. Tartaric acid in its D- and L-form and in the form of the racemate (pyruvic acid), is particularly suitable. Among the hydroxydi- and tricarboxylic acids containing asymmetry centers, both optical antipodes and also the racemates and, in the case of tartaric acid, the meso form are suitable. The hydroxydi- or tricarboxylic acids are added to the aqueous composition in a total quantity of from 0.5 to 5.5%, preferably 2 to 5%, most preferably 3 to 4%, by weight.

The pH value of the composition should be between 2 and 6, adjusted (if necessary) by suitable buffering agents.

The aqueous composition of step (E) may be made up in the form of a setting lotion, as a conditioner (antistat), as a hair lotion, or as an emulsion-like rinse. In addition to the characteristic components mentioned, it may contain any of the auxiliaries and additives typical of such preparations.

In the case of setting lotions, these are water-soluble polymers having a setting effect, such as polyvinylpyrrolidone and polyvinylpyrrolidone/vinyl acetate colpolymers, methyl and hydroxyethyl cellulose, carboxylmethyl cellulose, polyacrylic acids and water-soluble vegetable gums. Finally, lower alcohols, perfumes and perfume oil solubilizers may also be present.

Further components suitable for conditioners include setting additives, glucose, vitamins, protein derivatives, vegetable extracts, perfumes and perfume oil solubilizers.

Further components suitable for hair lotions include lower (especially $C_{2-6}$) alcohols, vegetable extracts, conventional cosmetic oil components, cationic surfactants, perfumes and perfume oil solubilizers.

Rinses having a caring and conditioning effect may contain fatty alcohols, such as cetyl and stearyl alcohol, fatty acid mono- and diglycerides, for example based on palmitic and stearic acid, cosmetic oil components, emulsifiers, cationic surfactants, such as for example cetyl trimethylammonium chloride or cetyl pyridinium chloride, and also perfumes as further components.

The aftertreatment composition is prefrably formulated as a conditioner which, in addition to the aluminium (III) salt and the hydroxydi- or tricarboxylic acid, contains a conditioning (i.e. antistatic, etc.) quaternary ammonium compound in a quantity of from 0.5 to 3% by weight. The nature of the quaternary ammonium compound is not critical, other than that it must be independently useful as a conditioner and still compatible with the required ingredients of this invention. Such compounds are well known in the art.

The aqueous preparations for carrying out the process accroding to the invention are applied in immediate succession to the mechanically shaped hair (fixed by curlers, rollers, and the like). The success of the aftertreatment therefore critically depends on the aftertreatment being carried out immediately after the oxidizing fixing step on the mechanically waved, curled hair. For this reason, it is of particular advantage to pack the various compositions for the inventive method in a single pack. In this way, it is possible to ensure with greated certainty, particularly for non-professional domestic application of the method, that the user employs preparations optimally adapted to one another in terms of quantity and concentration so that incorrect dosages are largely avoided. Accordingly, the present invention also comprises means for carrying out the entire permanent hair waving process, consisting essentially of the three spatially separate compositions accommodated in a single package, the first composition containing a keratin-reducing substance, the second composition an oxidizing agent and the third composition an aluminium (III) salt and a $C_{4-6}$ hydroxydi-or tricarboxylic acid, which is the inventive aftertreatment.

The following Examples illustrate the invention, and are merely representative without being limiting. All percentages in the examples are by weight, unless otherwise indicated.

| 1. Typical keratin-reducing composition | |
|---|---|
| Thioglycolic acid | 7.5% |
| Ammonia (conc. aqueous solution) | 9.0% |
| 1-hydroxyethane-1,1-diphosphonic acid | 0.3% |
| Castor oil ethoxylate (40 EO) | 3.0% |
| Nonylphenol ethoxylate (9 EO) | 3.0% |
| Ammonium carbonate | 1.0% |
| "Opacifier Permanent 601" (1) | 0.3% |
| Perfume oil | 0.5% |
| Water | q.s. ad 100.0% |

| 2. Typical oxidative fixing composition | |
| --- | --- |
| Potassium bromate | 3.5% |
| Tartaric acid | 0.15% |
| Coconut oil fatty acid diethanolamide | 5.0% |
| "Texapon" N 25 (2) | 25.0% |
| Perfume oil | 0.3% |
| Sodium chloride | 1.0% |
| Water | q.s. ad 100.0% |

Alternative aftertreatment compositions applied after the oxidative fixing of a permanent wave-treatment (INVENTIVE COMPOSITIONS):

| 3.1 Permanent-wave setting lotion | |
| --- | --- |
| "Luviskol" VA 64 (3) | 1.5% |
| Tartaric acid | 4.0% |
| AlCl$_3$ | 2.0% |
| Isopropanol | 40.0% |
| Perfume oil | 0.5% |
| Water | q.s. ad 100.0% |
| 3.2 Permanent-wave conditioner | |
| Castor oil ethoxylate (40 EO) | 0.2% |
| D-panthenol | 3.0% |
| Glucose | 3.0% |
| Citric acid | 3.0% |
| AlCl$_3$ | 3.0% |
| "Opacifier E 305" (1) | 0.1% |
| Perfume oil | 0.1% |
| Water | q.s. ad 100.0% |
| 3.3 Permanent-wave hair lotion | |
| "Cetiol" HE (4) | 1.0% |
| "Extrapon Birke Spezial" (5) | 1.0% |
| Malic acid | 3.0% |
| Al$_2$(SO$_4$)$_3$ | 2.0% |
| Isopropanol | 30.0% |
| Perfume oil | 0.3% |
| Water | q.s. ad 100.0% |
| 3.4 Permanent-wave rinse | |
| Cetyl/stearyl alcohol | 4.0% |
| Cetyl trimethylammonium chloride (25% aqueous solution) | 1.5% |
| AlCl$_3$ | 3.0% |
| Tartaric acid | 4.0% |
| Copaiva balsam oil | 0.4% |
| Perfume | 0.4% |
| Sodium lauryl sulfate | 1.0% |
| Water | q.s ad 100.0% |

The following commerical products and/or trademarks were used in the formulations:

(1) Styrene copolymer dispersion, opacifier (Morton Williams)
(2) Fatty alcohol-C$_{12-14}$-polyglycol ether (2 EO) sulfate, Na salt, 28% aqueous solution (Henkel KGaA)
(3) Vinlypyrrolidone/vinyl acetate (60:40) copolymer (BASF)
(4) Fatty acid ester of a glycerol ethoxylate, CTFA name: PEG-7-glyceryl cocoate (Henkel KGaA)
(5) Birch active-substance concentrate (Dragoco)

We claim:

1. A composition for the aftertreatment of hair during permanent waving, consisting essentially of:
   (i) at least one aluminum III salt which is water soluble, present in about 0.2 to 5.0% by weight;
   (ii) at least one hydroxydi-C$_{4-6}$-carboxylic acid or hydroxytri-C$_{4-6}$-carboxylic acid, present in about 0.5 to 5.5% by weight; and
   (iii) water, present in q.s. ad 100% by weight, all weights based upon the total aftertreatment composition.

2. The composition of claim 1 wherein:
   (i) is AlCl$_3$; AlCl$_3$ · 6 H$_2$O; Al(SO$_4$)$_4$; Al(SO$_4$)$_3$ · 18 H$_2$O; AlNa(SO$_4$)$_2$ · 12 H$_2$O; Al(NH$_4$)(SO$_4$)$_2$ · 12 H$_2$O; aluminum lactate, aluminum acetate, or a mixture thereof.

3. The composition of claim 1 wherein:
   (i) is AlCl$_3$, Al(SO$_4$)$_3$, or a mixture thereof.

4. The composition of claim 1 wherein:
   (ii) is malic acid, tartaric acid, citric acid, or a mixture thereof 5. The composition of claim 2 wherein:
   (ii) is malic acid, tartaric acid, citric acid, or a mixture thereof.

6. The composition of claim 3 wherein:
   (ii) is malic acid, tartaric acid, citric acid, or a mixture thereof.

7. The composition of claim 1 wherein:
   (i) is AlCl$_3$; and
   (ii) is tartaric acid.

8. The composition of claim 1 wherein:
   (i) is present in about 1 to 4% by weight; and
   (ii) is present in about 2 to 5% by weight.

9. The composition of claim 5 wherein:
   (i) is present in about 1 to 4% by weight; and
   (ii) is present in about 2 to 5% by weight.

10. The composition of claim 1 wherein
    (i) is present in about 2 to 3% by weight; and
    (ii) is present in about 3 to 4% by weight.

11. The composition of claim 6 wherein
    (i) is present in about 2 to 3% by weight; and
    (ii) is present in about 3 to 4% by weight.

12. The composition of claim 1, having a pH of about 2 to 6.

13. A method for the permanent waving of hair, comprising:
    (A) applying to said hair an aqueous composition comprising an effective amount of a keratin-reducing substance;
    (B) shaping said hair with mechanical means before and/or after step (A);
    (C) rinsing said hair with water after said keratin is effectively reduced
    (D) fixing said hair by applying a composition comprising an effective amount of an oxidizing agent;
    (E) aftertreating the fixed hair by applying thereto the composition of claim 1, in an aftertreating-effective amount;
    (F) rinsing said aftertreated hair, and
    (G) removing said mechanical means from said hair.

14. The method of claim 13 wherein said keratin-reducing substance comprises an alkali or ammonium thioglycolate or thiolactate.

15. The method of claim 13 wherein said oxidizing agent comprises potassium bromate, sodium bromate, or hydrogen peroxide.

16. The method of claim 14 wherein said oxidizing agent comprises potassium bromate, sodium bromate, or hydrogen peroxide.

* * * * *

UNITED STATES PATENT AND TRADEMARK OFFICE
CERTIFICATE OF CORRECTION

PATENT NO. : 4,834,971

DATED : May 30, 1989

INVENTOR(S) : Adolf Klenk, Detlef Hollenberg, Horst Hoeffkes

It is certified that error appears in the above-identified patent and that said Letters Patent is hereby corrected as shown below:

On the cover page, at item (30), for the priority date indicated as "Aug. 16, 1987", read --Aug. 16, 1986--.

In Claim 2, at Col. 6, line 6, "$Al(SO_4)_4$" should read --$Al(SO_4)_3$--.

Signed and Sealed this

Seventeenth Day of April, 1990

Attest:

HARRY F. MANBECK, JR.

*Attesting Officer*     *Commissioner of Patents and Trademarks*